(12) United States Patent
Epstein (10) Patent No.: US 12,419,635 B2
(45) Date of Patent: Sep. 23, 2025

(54) SUTURE GUIDE

(71) Applicant: David H. Epstein, Fort Lauderdale, FL (US)

(72) Inventor: David H. Epstein, Fort Lauderdale, FL (US)

( * ) Notice: Subject to any disclaimer, the term of this patent is extended or adjusted under 35 U.S.C. 154(b) by 0 days.

(21) Appl. No.: 18/963,033

(22) Filed: Nov. 27, 2024

(65) Prior Publication Data
US 2025/0261936 A1   Aug. 21, 2025

Related U.S. Application Data (60) Provisional application No. 63/554,837, filed on Feb. 16, 2024.

(51) Int. Cl.
*A61B 17/04* (2006.01)

(52) U.S. Cl.
CPC ................... *A61B 17/0482* (2013.01)

(58) Field of Classification Search
CPC . A61B 17/0482; A61B 17/17; A61B 17/3403; A61B 2017/22069; A61M 25/02; A61M 2025/0286
USPC .......................................................... 606/148
See application file for complete search history.

(56) References Cited

U.S. PATENT DOCUMENTS

| | | | | |
|---|---|---|---|---|
| 4,798,595 | A * | 1/1989 | Andersson | A61M 5/32 604/174 |
| 2012/0265223 | A1* | 10/2012 | Shpaichler | A61B 17/0482 606/148 |
| 2014/0371537 | A1* | 12/2014 | Marczyk | A61B 17/3462 600/204 |
| 2015/0005733 | A1* | 1/2015 | Le | A61M 25/02 604/174 |
| 2018/0272056 | A1 | 9/2018 | Peh et al. | |
| 2018/0289939 | A1 | 10/2018 | Mason et al. | |
| 2019/0321594 | A1 | 10/2019 | Gilliland et al. | |
| 2022/0134075 | A1 | 5/2022 | Tal | |
| 2023/0032423 | A1 | 2/2023 | Fedor et al. | |

OTHER PUBLICATIONS

Krenik et al. "Catheter Securement Systems for Peripherally Inserted and Nontunneled Central Vascular Access Devices", Journal of Infusion Nursing, Jul. 2016; 39(4): 210-217.
Spencer et al., (Sep. 2018). "Securing vascular access devices," American Nurse Today, vol. 19, No. 19; pp. 29-31.
"How to: Perclose ProGlide Single Device Deployment," YouTube, uploaded by Abbott Cardiovascular, Oct. 14, 2020, retrieved at <https://youtu.be/QkcJcu3aVwQ>.

* cited by examiner

*Primary Examiner* — Dianne Dornbusch
(74) *Attorney, Agent, or Firm* — Michele V. Frank; Venable LLP (57) ABSTRACT

A suture guide for securing a catheter to a patient includes a body and a needle channel extending through the body. The needle channel includes a first passage extending from a first passage inlet to a first passage outlet, and a second passage extending from a second passage inlet a second passage outlet. The first passage is curved toward the second passage as the first passage extends from the first passage inlet to the first passage outlet. The first passage is configured to guide a suture needle from the first passage outlet to the second passage inlet such that the suture needle exits the first passage, traverses skin and tissue of a patient to create a patient suture passage between the first passage and the second passage, and enters the second passage to secure the catheter to the patient.

19 Claims, 5 Drawing Sheets

SUTURE GUIDE

CROSS-REFERENCE TO RELATED APPLICATIONS

This application claims priority to U.S. Provisional Application No. 63/554,837, filed Feb. 16, 2024, the entire contents of which are incorporated herein by reference.

TECHNICAL FIELD

The present disclosure relates to a suture guide, for example, for securing a catheter to a patient.

BACKGROUND

Intravenous catheters and other devices for subcutaneous access are sutured or adhered to a patient to maintain the catheter or device in the proper location. To suture the device to the patient, suture wings are provided on the catheter to provide location to suture the catheter or device to the patient.

BRIEF SUMMARY

A suture guide for securing a catheter to a patient, the suture guide comprising a body having an upper surface, a lower surface, a first side surface extending between the upper surface and the lower surface, and a second side surface extending on an opposing side of the body between the upper surface and the lower surface, and a needle channel extending through the body, the needle channel comprising a first passage extending from a first passage inlet to a first passage outlet, and a second passage extending from a second passage inlet a second passage outlet, wherein the first passage is curved toward the second passage as the first passage extends from the first passage inlet to the first passage outlet, and wherein the first passage is configured to guide a suture needle from the first passage outlet to the second passage inlet such that the suture needle exits the first passage, traverses skin and tissue of a patient to create a patient suture passage between the first passage and the second passage, and enters the second passage to secure the catheter to the patient.

A catheter assembly comprising a catheter; and a suture guide coupled to the catheter, the suture guide comprising a body having an upper surface, a lower surface, a first side surface extending between the upper surface and the lower surface, and a second side surface extending on an opposing side of the body between the upper surface and the lower surface, and a needle channel extending through the body, the needle channel comprising a first passage on a first side of the catheter and extending from a first passage inlet to a first passage outlet, and a second passage on a second side of the catheter extending from a second passage inlet a second passage outlet, wherein the first passage is curved toward the second passage as the first passage extends from the first passage inlet to the first passage outlet, and wherein the first passage is configured to guide a suture needle from the first passage outlet to the second passage inlet such that the suture needle exits the first passage, traverses skin and tissue of a patient to create a patient suture passage between the first passage and the second passage, and enters the second passage to secure the catheter to the patient.

A suture guide for securing a catheter to a patient, the suture guide comprising a body having an upper surface, a lower surface, a first side surface extending between the upper surface and the lower surface, and a second side surface extending on a opposing side of the body between the upper surface and the lower surface and a needle channel. The needle channel includes a first passage extending from a first passage inlet to a first passage outlet and a second passage separate from the first passage, the second passage extending from a second passage inlet a second passage outlet. The needle channel is configured to guide a suture needle from the first passage inlet to the second passage outlet such that the suture needle traverses skin and tissue of a patient between the first passage and the second passage and such that a contour of the first passage, a contour of the second passage, and a contour of the tissue traversed by the suture needle is the same as a contour of the suture needle.

A catheter assembly comprising a catheter and a suture guide coupled to the catheter, the suture guide having a needle tract configured to guide a suture needle from a first side of the catheter to a second, opposing side of the catheter. The needle tract is configured to guide the suture needle through the suture guide and through a patient's skin to secure the catheter to the patient's skin.

A method for securing a catheter to a patient, the method comprising locating a suture guide on a skin surface of the patient, inserting a suture needle with suture material affixed thereto into the suture guide, guiding the suture needle from a first side of the suture guide to a second, opposing side of the suture guide, wherein the first side and the second, opposing side are both located above the skin surface of the patient, and securing the suture material such that the suture guide is secured to the skin surface of the patient.

BRIEF DESCRIPTION OF THE DRAWINGS

The foregoing and other features and advantages will be apparent from the following, more particular, description of various exemplary embodiments, as illustrated in the accompanying drawings, wherein like reference numbers generally indicate identical, functionally similar, and/or structurally similar elements.

DETAILED DESCRIPTION

Various embodiments are discussed in detail below. While specific embodiments are discussed, this is done for illustration purposes only. A person skilled in the relevant art will recognize that other components and configurations may be used without departing from the spirit and scope of the present disclosure.

As used herein, the terms "first," "second," and "third" may be used interchangeably to distinguish one component from another and are not intended to signify location or importance of the individual components.

The terms "upper," "lower," "left," and "right" refer to relative positions of a sensor pod with respect to a ground surface, as viewed from a position forward of the sensor pod. For example, "upper" refers to a position vertically above a "lower" position. For example, "left" refers to a position laterally to the left of a "right" position.

The term "side" as used herein may refer to a surface, wall, edge, border, boundary, etc., or simply to a general position or location with respect to the described component (e.g., not referring to any physical component).

The terms "coupled," "fixed," "attached," "connected," and the like, refer to both direct coupling, fixing, attaching, or connecting as well as indirect coupling, fixing, attaching, or connecting through one or more intermediate components or features, unless otherwise specified herein.

The singular forms "a," "an," and "the" include plural references unless the context clearly dictates otherwise.

The suture guide of the present disclosure provides a system and method for securing a catheter to a skin surface of a patient. The suture guide of the present disclosure simplifies and enhances the safety of securing vascular catheters to the skin surface of a patient. Prior art methods and devices include providing two separate sutures on either side of a catheter hub using suture wings. This is difficult for the operator, particularly, where the available skin space is small such that placing the two sutures correctly is difficult, can take longer than the process of putting the catheter in, and engenders a significant risk of a fingerstick while threading the suture needle while holding the catheter in place.

Accordingly, the suture guide of the present disclosure provides an attachment or addition to the back of the catheter or catheter hub that has a channel (referred to herein as a passage) to receive the suture needle. The channel, by the nature of the shape of the channel, directs the suture needle from a first passage of the channel, under the skin behind the catheter hub, to the corresponding second passage of the channel on the opposite side of the catheter. The suture guide of the present disclosure thus has a predetermined angle and shape of the channel and openings to the channel that will create a needle tract of the appropriate depth below the skin surface. In addition, the back end of the suture material may be pre-knotted, or have a bumper, so that at least the first side requires no further fixation (e.g., the operator does not need to secure or knot the suture material at a first end). The needle end of the suture would be clipped above the catheter hub surface, in some examples, this may be a small, vascular-type clip applied to the free end of the suture material, followed by the removal of the excess suture material.

FIGS. 1 to 4 illustrate exemplary suture guides to achieve the aforementioned function, however, the present disclosure is not limited to the appearance of the suture guide illustrated and other shapes, orientations, sizes, contours, curves, angles, etc., are contemplated. The suture guide of the present disclosure provides a track for a suture needle from one side of the catheter to the other. In some examples, the present disclosure provides a two-part device: the suture guide and the catheter. In such an example, the suture guide may be first secured to the skin surface, and then attached or snapped onto the back of the catheter. In another example, the suture guide is integral with and unitary to the catheter hub.

Figure 1:
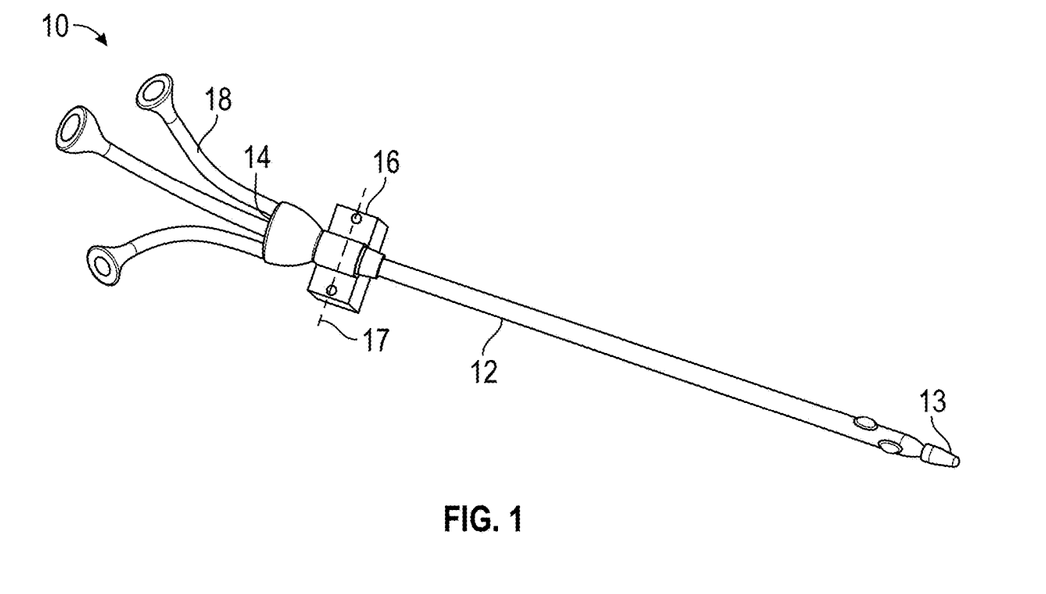
FIG. 1 illustrates an exemplary catheter, according to the present disclosure.

Referring to FIG. 1, a catheter 10 includes an elongated catheter shaft 12 having a tip 13 and a catheter hub 14 that may admit one or more fluid access lines 18 through the catheter shaft 12 and into a patient (not shown) in a conventional manner. During use of the catheter 10, and prior to any procedure being performed on the patient, the tip 13 is inserted into the patient and the catheter 10 is secured to the outer surface (e.g., skin) of the patient, typically with one or more sutures. In FIG. 1, a suture guide 16 is associated with the catheter 10 to allow for securing of the catheter 10 to the patient. The suture guide 16 has a longitudinal centerline axis 17. In practice, a suture material is inserted through the openings of the suture guide 16 to secure the suture guide 16 (and, therefore, also the catheter hub 14 and catheter shaft 12) to the patient.

FIGS. 2A to 2F illustrate schematic views of an exemplary suture guide 100 that may be employed as the suture guide 16 in FIG. 1. The suture guide 100 may be integrally and unitarily formed with the catheter 10 or may be separately formed and attached to the catheter 10. For example, when integrally formed with the catheter 10, the suture guide 100 and the catheter 10 may be molded or manufactured together as a single unitary component. When coupled or connected, the catheter 10 and the suture guide 100 may be attached in any number of manners, including snap connections, adhesive, and other coupling types. As illustrated in FIG. 1, the suture guide 100 may be integral with or coupled to the catheter hub 14, however, other locations along the catheter shaft 12 are contemplated.

Figure 2A:
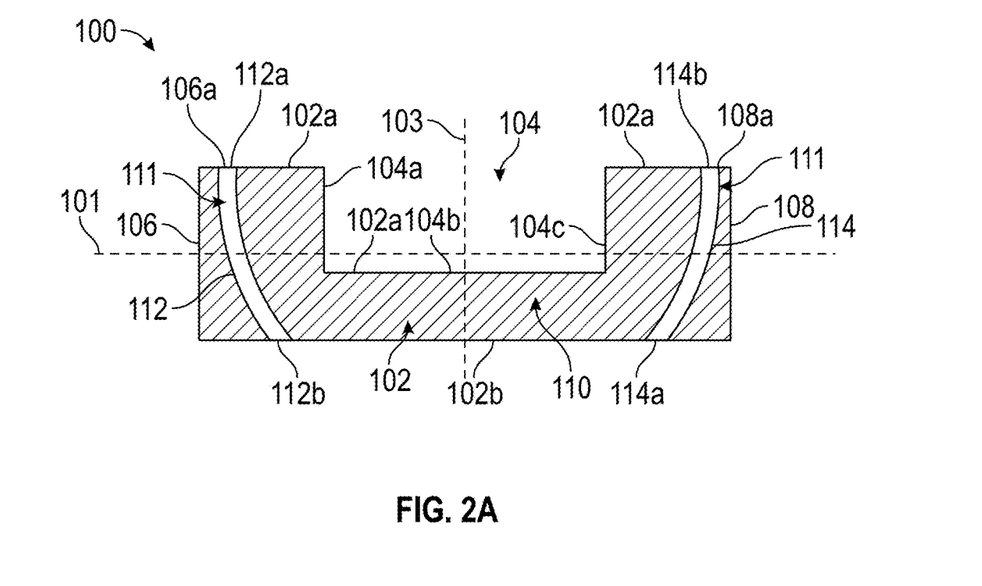
FIG. 2A illustrates a cross-sectional view of an exemplary suture guide, taken through a longitudinal centerline axis of the suture guide, according to the present disclosure.

The suture guide 100 of FIG. 2A is illustrated from a side, cross-sectional view, taken at a longitudinal centerline axis 101 of the suture guide 100. The suture guide 100 includes a body 102 having the longitudinal centerline axis 101 and a vertical centerline axis 103 that is normal to the longitudinal centerline axis 101. The body 102 is shown schematically in FIG. 2A and is not limited to the generally u-shaped and rectangular shape shown. Other shapes, such as polygonal, curved, ovular, circular, etc., are contemplated. The body 102 includes a groove 104 for receiving the catheter shaft 12 (FIG. 1) or the catheter hub 14 (FIG. 1) to couple the suture guide 100 to the catheter 10. The groove 104 is optional and may be omitted (e.g., as described with respect to the suture guide 300 of FIGS. 3A and 3B). The body 102 includes a first portion 106, a second portion 108, and a third portion 110. The third portion 110 extends between the first portion 106 and the second portion 108. The first portion 106 and the second portion 108 protrude outwardly from the third portion 110. That is, the first portion 106 and the second portion 108 are raised with respect to the third portion 110. The raised or protruding nature of the first portion 106 and the second portion 108 form the groove 104. Although the first portion 106 and second portion 108 are shown as rectangular, other shapes are contemplated. Likewise, the shape of the groove 104 may be different than shown. For example, the sides 104a, 104b, 104c of the groove 104 may be curved or otherwise of a conforming or mating shape to a body of the catheter 10 (FIG. 1) to allow for a mating connection or interface between the catheter 10 and the suture guide 100.

FIG. 2A further illustrates a channel, also referred to as a needle channel 111, in the body 102 of the suture guide 100. The needle channel 111 has a first passage 112 and a second passage 114. The first passage 112 extends between an upper surface 102a of the body 102 to a lower surface 102b of the body 102. In the example shown in FIG. 2A, the portion of upper surface 102a through which the first passage 112 extends is an upper surface 106a of the first portion 106. The second passage 114 extends between the upper surface 102a of the body 102 to the lower surface 102b of the body 102. In the example shown in FIG. 2A, the portion of upper surface 102a through which the second passage 114 extends is an upper surface 108a of the second portion 108. Together, the first passage 112 and the second passage 114 form the needle channel 111 through which a suture needle and a suture material are installed to secure the suture guide 100 (and thus the catheter 10) to the patient, as described in more detail with respect to FIGS. 2D to 2F.

Figure 2B:
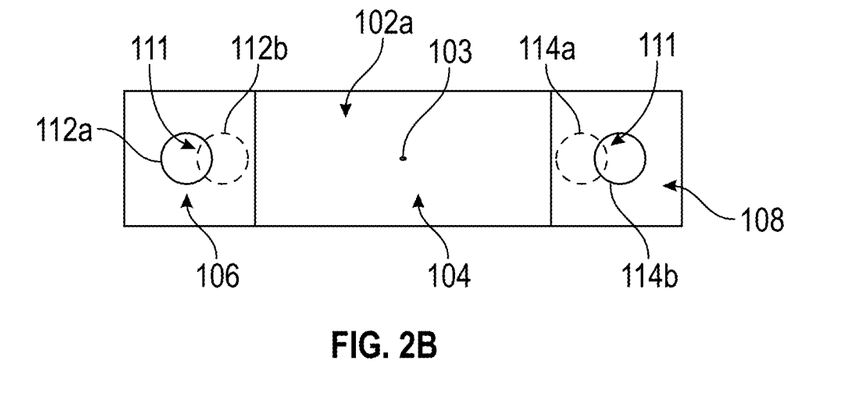
FIG. 2B illustrates a top view of the suture guide of FIG. 2A, according to the present disclosure.
Figure 2C:
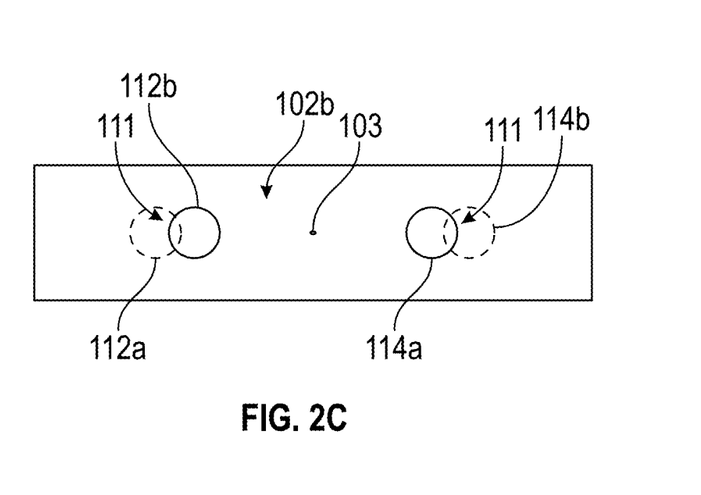
FIG. 2C illustrates a bottom view of the suture guide of FIG. 2A, according to the present disclosure.

Referring to FIGS. 2A to 2C, the first passage 112 extends from a first passage inlet 112a to a first passage outlet 112b. The first passage inlet 112a extends through the upper surface 102a of the body 102 and the first passage outlet 112b extends through the lower surface 102b of the body 102. The first passage 112 provides guidance for a suture needle 200 (FIG. 2D) to extend from the first passage inlet 112a to the first passage outlet 112b. Thus, the first passage inlet 112a, the first passage 112, and the first passage outlet 112b are sized and shaped as a guide for the suture needle 200. The shape, contour, or profile of the first passage 112 may be the same or similar as that of the suture needle 200, but larger than the outer diameter of the suture needle to accommodate passage therethrough. By having the same or similar shape, contour, or profile, the first passage 112 acts as a guide for the suture needle 200 causing the suture needle 200 to proceed through the first passage 112 along a predetermined pathway (defined by the shape and curvature of the first passage 112). In this manner, the suture needle 200 will be caused to exit the first passage outlet 112b and enter the patient at a predetermined location (e.g., the inlet to the second passage 114, as discussed in more detail to follow). In this manner, the suture needle 200 is obligated to move from the first passage 112 to the second passage 114 due to the contouring of the first passage 112.

With continued reference to FIGS. 2A to 2C, the second passage 114 extends from a second passage inlet 114a to a second passage outlet 114b. The second passage inlet 114a extends through the lower surface 102b of the body 102 and the second passage outlet 114b extends through the upper surface 102a of the body 102. The second passage 114 provides guidance for the suture needle 200 (FIG. 2D) to extend from the second passage inlet 114a to the second passage outlet 114b. Thus, the second passage inlet 114a, the second passage 114, and the second passage outlet 114b are sized and shaped as a guide for the suture needle 200. As with the first passage 112, the shape of the second passage 114 may be the same or similar shape, contour, or profile as the suture needle 200, but larger than the outer diameter of the suture needle to accommodate passage therethrough. This may result in the first passage 112 and the second passage 114 being mirror images of each other. In particular, the first passage 112 is arcuate. The first passage 112 is curved toward the second passage 114 as the first passage 112 extends from the first passage inlet 112a to the first passage outlet 112b. Thus, a distance from the first passage outlet 112b to the vertical centerline axis 103 is less than a distance from the first passage inlet 112a to vertical centerline axis 103. In other words, the first passage outlet 112b is closer to the vertical centerline axis 103 (and to the second passage 114) than the first passage inlet 112a.

Similarly, the second passage 114 is arcuate. The second passage 114 is curved away from the first passage 112 as the second passage 114 extends from the second passage inlet 114a to the second passage outlet 114b. Thus, a distance from the second passage inlet 114a to vertical centerline axis 103 is less than a distance from the second passage outlet 114b to the vertical centerline axis 103. In other words, the second passage inlet 114a is closer to the vertical centerline axis 103 (and to the first passage 112) than the second passage outlet 112b. In this way, the first passage 112 and the second passage 114 are convex. By having the same or similar shape, contour, or profile, the second passage 114 acts as a guide causing the suture needle 200 to proceed through the second passage 114 along a predetermined pathway defined by the shape and curvature of the second passage 114. In this manner, once inserted into the first passage 112, the suture needle 200 is caused or forced to follow through from the first passage 112 to the second passage 114 due to the mating profile. In this way, the first passage 112 curves the suture needle 200 and directs the suture needle 200 through a patient 50 (e.g., tissue of the patient 50) and to the second passage 114, as detailed further below.

As illustrated in FIGS. 2B and 2C, the first passage inlet 112a, the first passage outlet 112b, the second passage inlet 114a, and the second passage outlet 114b each the same dimension (e.g., diameter) of opening. In some examples, the first passage outlet 112b may have a larger dimension (e.g., diameter) than the first passage inlet 112a and the second passage inlet 114a may have a larger dimension (e.g., diameter) than the second passage outlet 114b. In the examples where the inlets and outlets have differing dimensions (e.g., diameters), the passages may also increase (the first passage 112) or decrease (the second passage 114) in dimension from inlet to outlet. Such an increase or decrease in dimension of passage and passage inlet/outlet facilitates guiding and exiting of the suture needle 200 from the body 102. Although illustrated and described with circular cross-sections, the passage inlets 112a, 114a, the passages 112, 114, and the passage outlets 112b, 114b may have other shape cross-sections, such as, for example, but not limited ovals and polygons. Regardless of the size, structure, shape, or dimension of the passage, passage inlets, or passage outlets, the passages are arranged to facilitate capture of the suture needle 200 during installation of the suture material.

In some examples, the first passage inlet 112a and the second passage outlet 114b are identical and the first passage outlet 112b and the second passage inlet 114a are identical. In such an example, the suture guide 100 is symmetric about the vertical centerline axis 103 extending from the upper surface 102a to the lower surface 102b. In this example, therefore, the second passage outlet 114b may operate as an inlet and the first passage inlet 112a may operate as an outlet such that a suture guide may be inserted from either side of the suture guide 100. In other examples, the suture guide 100, passages, protruding portions (e.g., first portion 106, second portion 108), groove, or any combination thereof may be arranged such the suture guide 100 is not symmetric about the vertical centerline axis 103 extending from the upper surface 102a to the lower surface 102b.

The first passage 112 and the second passage 114 are separate, with separate inlets and outlets. The first passage 112 and the second passage 114 do not intersect. The first passage inlet 112a of the first passage 112 is on the same surface as the second passage outlet 114b of the second passage 114, though that surface may be non-planar. The first passage outlet 112b of the first passage 112 is on the same surface as the second passage inlet 114a of the second passage 114, though that surface may be non-planar. Although shown on the upper surface and lower surface, the inlets and outlets of the passages may be on different surfaces, such as shown and described with respect to FIG. 4.

Figure 2D:
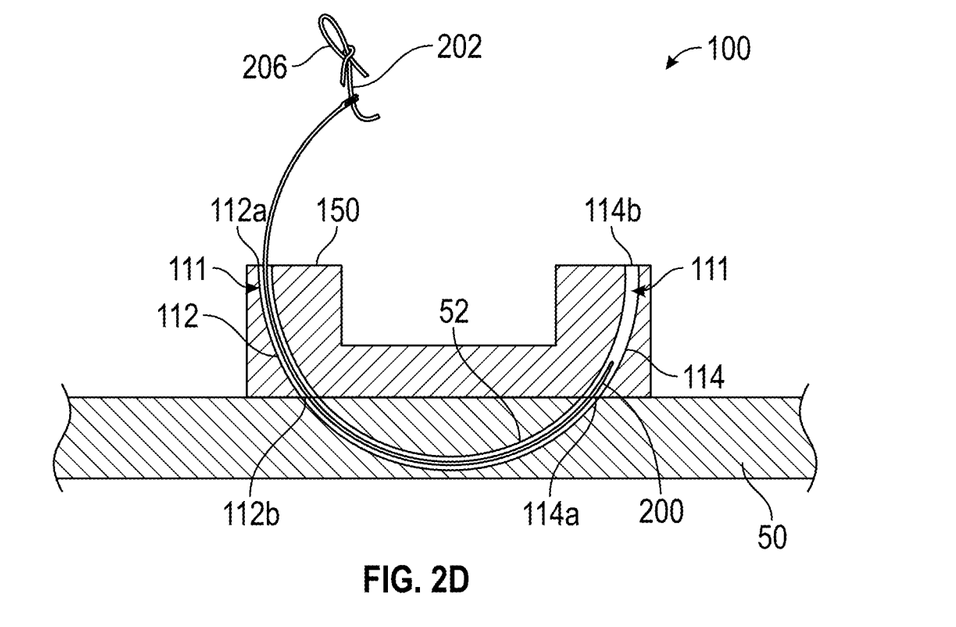
FIG. 2D illustrates a cross-sectional view of the suture guide of FIG. 2A with a suture needle partially installed therein, according to the present disclosure.
Figure 2E:
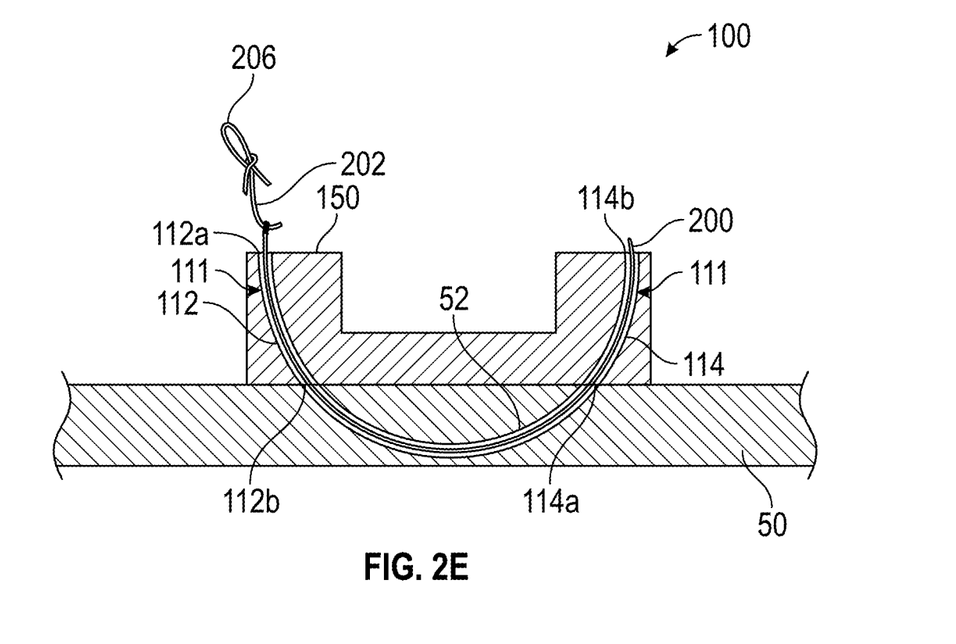
FIG. 2E illustrates a cross-sectional view of the suture guide of FIG. 2A with the suture needle of FIG. 2D fully installed therein, according to the present disclosure.
Figure 2F:
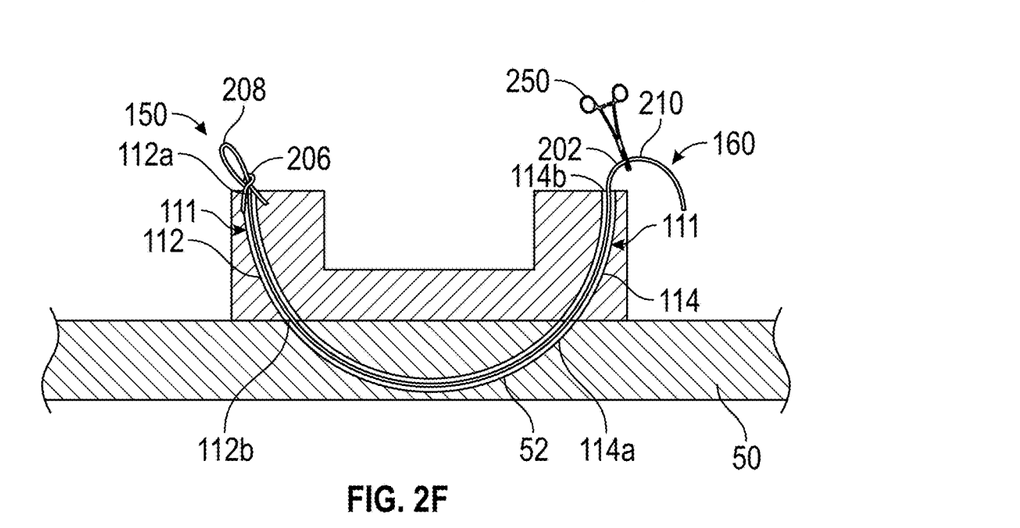
FIG. 2F illustrates a cross-sectional view of the suture guide of FIG. 2A with the suture material, coupled to the suture needle of FIG. 2E, fully installed therein, according to the present disclosure.

FIGS. 2D to 2F illustrate insertion of the suture needle 200 and a suture material 202, such as a suture thread, into the suture guide 100 to secure the suture guide 100 (and thus the catheter 10) to the patient 50. Since the first passage 112 has the same or similar shape or contour as the suture needle 200, when the suture needle 200 is inserted through the first passage inlet 112a by the user, the suture needle 200 is caused to travel through the first passage 112, as shown in FIG. 2D, at the predetermined contour of the first passage 112 and exit the first passage 112 from the first passage outlet 112b into the patient 50 at a predetermined location. The contour or shape of the first passage 112 also causes the suture needle 200 to continue through the patient 50 and into the second passage inlet 114a of the second passage 114 at the same predetermined contour. In particular, the first passage 112 directs the suture needle 200 from the first passage inlet 112a into the patient 50 through the first passage outlet 112b. Once the suture needle 200 has been inserted into the patient 50, the curvature of the first passage 112 directs the suture needle 200 into the patient 50 and then to the second passage inlet 114a of the second passage 114. The second passage 114 directs the suture needle 200 from the second passage inlet 114a out of the second passage 114 through the second passage outlet 114b.

As illustrated in FIG. 2E, the suture needle 200 is sized such that an end protrudes from the first passage inlet 112a of the first passage 112 at the same time as a tip protrudes from the second passage outlet 114b of the second passage 114. The suture needle 200 must be sized longer than the total passage length (e.g., the length of passages 112, 114 and the portion of the patient 50 traversed) in order for the user to be able to push the end of the suture needle 200 through the first passage 112 and the second passage 114. Once the suture needle 200 exits the second passage 114, the tip of the suture needle 200 is exposed and the user can grab the tip to pull the suture needle 200 out of the suture guide 100. The suture guide 100 therefore provides a predetermined pathway through the patient 50 for the suture needle 200 to secure the suture guide 100 to the patient with a single suture thread or single suture material 202.

FIG. 2F illustrates the suture needle 200 removed and the suture material 202 fully inserted into both the suture guide 100 and the patient 50. As shown in FIG. 2F, the suture material 202 has the same contour as the suture needle 200 and the passages 112, 114. Once the suture needle 200 is removed and the suture material 202 is inserted, a tool 250 may grab an end (e.g., a second end 210) and tension applied to suture material 202 (due to a first securing device 206 at a first end 208). With the suture material 202 under tension, a clip (such as a clip 318 in FIG. 3B), may be secured to the second end 210 the suture material 202. The clip and the first securing device 206 secure the suture guide 100 to the patient 50, and, thus, secure the catheter 10 (FIG. 1) to the patient 50.

As illustrated in FIGS. 2D to 2F, the suture material 202 is coupled to the suture needle 200 and extends through the patient 50 (this may be the skin of the patient 50 or other organ to which the suture is being applied). The suture needle 200 and suture material 202 are guided through the patient 50 (e.g., through a contour, also referred to as a patient suture passage 52). Accordingly, the first passage 112, the second passage 114, and the patient suture passage 52 through the patient 50 provide a tract or contour, also referred to as a needle tract, for guiding the suture needle 200 from a first side 150 (e.g., the inflow side) of the suture guide 100 to a second side 160 (e.g., the outflow side) of the suture guide 100. The patient suture passage 52 through the patient 50 is not a preformed passage or channel within the patient 50. Rather, the patient suture passage 52 is the pathway the suture needle 200 is caused to travel due to the contour and shape of the first passage 112 and the second passage 114. The patient suture passage 52 has a contour that is the same as the suture needle 200. In this way, the contour of the patient suture passage 52 is the same as the contour of the first passage 112 and the second passage 114.

The suture guide 100, by way of the passages 112 and 114, allows for the suture needle 200 to be inserted in the first side 150 of the suture guide 100 (e.g., the first passage inlet 112a) and exit the other, second side 160 of the suture guide 100 (e.g., the second passage outlet 114b) with a single action by the operator. That is, the user need only insert the suture needle 200 into the first passage inlet 112a and the suture needle 200 is automatically guided from the first passage inlet 112a, through the patient 50, and to the second passage outlet 114b. The automatic guidance is due to the shape and size of the passages, inlets, and outlets. In this manner, a single suture is created to secure the suture guide 100 (and any device connected thereto) to the patient 50.

Since the suture material 202 is attached to the suture needle 200, the suture material 202 is guided through the suture guide 100 along with the suture needle 200. Thus, once the suture needle 200 and the suture material 202 have exiting the second passage 114, the suture guide 100 is attached to the patient 50 by way of the suture material 202. The suture material 202 is secured at both the first passage inlet 112a (with first securing device 206 at a first end 208) and the second passage outlet 114b (with a clip at a second end 210) to secure the suture guide 100 to the patient 50 and prevent removal of the suture guide 100 from the patient 50. As noted previously, a device, such as a catheter, may be located within the groove 104 (FIG. 2A) of the suture guide 100. Accordingly, once the suture guide 100 is secured to the patient 50, the catheter 10 may be secured to the patient 50 by locating the catheter in the groove 104 (either before securing of the suture guide 100 to the patient 50 or after securing of the suture guide 100 to the patient 50).

The first securing device 206 may be a knot, a bumper, a protrusion, or other device or means that is part of or coupled to the suture material 202 and that prevents removal of the suture material 202 from the suture guide 100 (e.g., by preventing a first end 208 of the suture material 202 from being pulled out of the suture guide 100 by tension of a second end 210 of the suture material 202 at the second (outflow) side 160). The first securing device 206 may be pre-formed, pre-tied, or pre-attached to the suture material 202 such that the suture material 202 is provided with the first securing device 206 before securing of the suture guide 100 to the patient 50 and before inserting the suture needle 200 into the suture guide 100. Once the suture material 202 is extended through the first passage 112 and the second passage 114, a second securing device (not shown, such as clip 318) be applied to the second end 210 of the suture material 202. The second end 210 is outside of the second passage 114 and above the upper surface 102a (FIG. 2B) of the suture guide 100. The second securing device at the second end 210 prevents the suture material 202 from being removed from the suture guide 100 (e.g., by preventing the second end 210 of the suture material 202 from being pulled out of the suture guide 100 by tension of the first end 208 of the suture material 202 at the first (inflow) side 150). With securing device at each of the first end 208 and the second end 210, the suture material 202 is prevented from being removed from the suture guide 100. Thus, the suture guide 100, and attached catheter 10, is secured to the patient 50.

In some examples, the suture guide 100 and the catheter 10 are simultaneously secured to the patient 50. In some examples, the catheter 10 is removably connected to the suture guide 100. In such examples, the catheter 10 may be inserted into the groove 104 before securing of the suture guide 100 on the patient 50 or after securing of the suture guide 100 on the patient 50.

As discussed, the shape and structure of the suture guide 100 is exemplary. Other shapes, dimensions, and sizes are contemplated so long as the passage through the suture guide allows for a suture needle to be guided from an upper surface on a first side of the suture guide, through the lower surface at a first location, through the patient, into the lower surface at a second location and out the upper surface on a second side (e.g., an opposing side of the suture guide from the first side, where a device may be coupled to the suture guide therebetween).

Figure 3A:
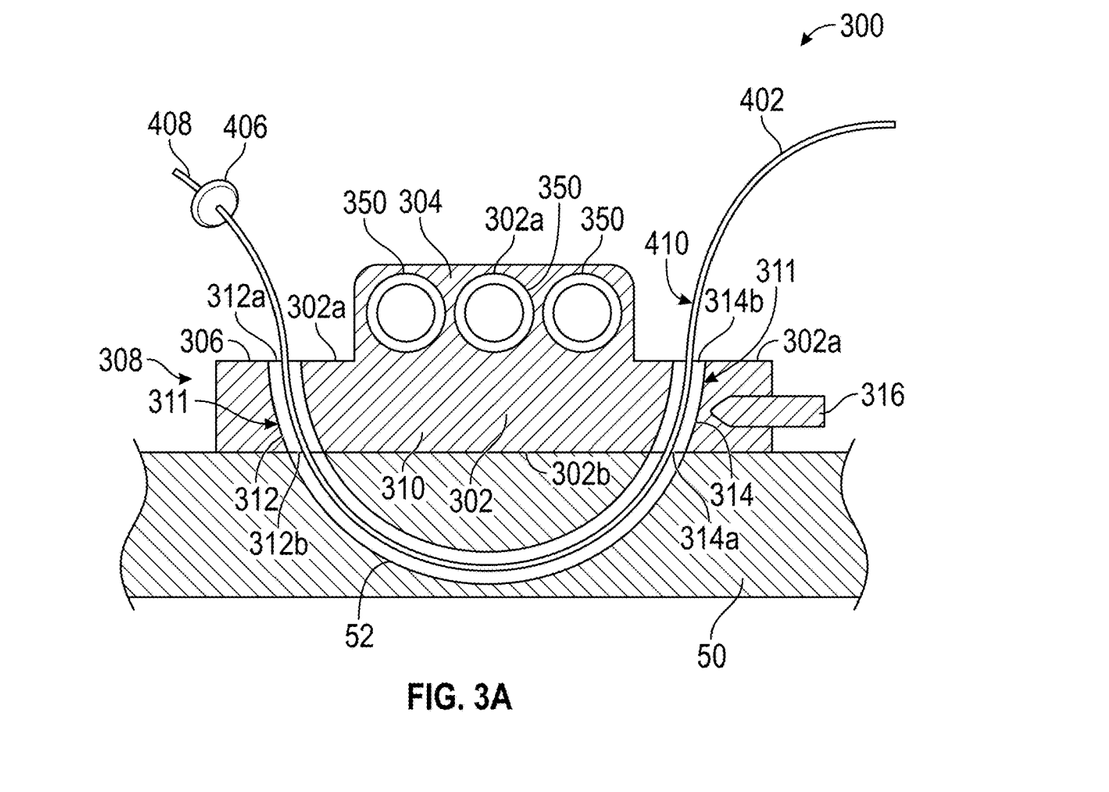
FIG. 3A illustrates a cross-sectional view of an exemplary suture guide with a suture material installed therein, taken through a longitudinal centerline axis of the suture guide, according to the present disclosure.
Figure 3B:
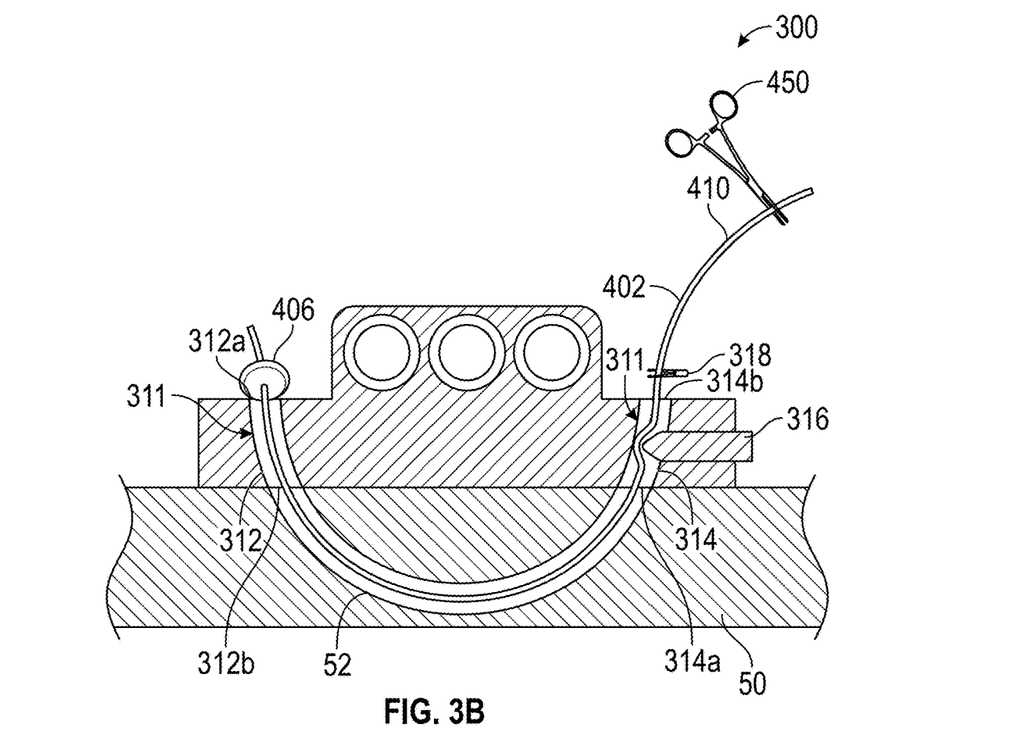
FIG. 3B illustrates the suture guide of FIG. 3A with the suture material secured within the suture guide, according to the present disclosure.

Accordingly, schematic views of another exemplary suture guide 300 that may be employed as the suture guide 16 in FIG. 1 are illustrated in FIGS. 3A and 3B. FIG. 3A illustrates a condition with the suture material 402 inserted within the suture guide 300 but not yet secured therein. FIG. 3B illustrates a condition with the suture material 402 secured within the suture guide 300. The same variations and alternatives described above with respect to the suture guide 100 of FIGS. 2A to 2F apply to the suture guide 300 as well. Likewise, the function, operation, and securement of the suture guide 300 is the same as the suture guide 100, unless otherwise noted in the description to follow. FIGS. 3A and 3B illustrate a cross-sectional view of the suture guide 300. A series of three openings 350 are illustrated in the suture guide 300. These openings 350 represent the fluid access lines 18 (FIG. 1). Therefore, the suture guide 300 illustrates a unitary suture guide 300 and catheter 10, however, as discussed previously, the catheter 10 may be separate from the suture guide 300 and may be coupled thereto.

The suture guide 300 includes a body 302. The body 302 is shown schematically in FIG. 3A and is not limited to the polygonal shape shown. Other polygonal shapes, such as curved, ovular, circular, etc., are contemplated. The body 302 includes a protrusion 304, which is the integral portion of the catheter 10. Alternatively, a groove, such as the groove 104, may be provided to receive the catheter 10. The protrusion 304 is optional and may be omitted. The body 302 includes a first portion 306, a second portion 308, and a third portion 310. The third portion 310 extends between the first portion 306 and the second portion 308. The third portion 310 may include the protrusion 304. Although the first portion 306, the second portion 308, and the third portion 310 are shown as rectangular, other shapes are contemplated.

Similar to the suture guide 100, the suture guide 300 includes a needle channel 311 formed of a first passage 312 and a second passage 314 in the body 302 of the suture guide 300. The first passage 312 extends between an upper surface 302a of the body 302 to a lower surface 302b of the body 302. The second passage 314 extends between the upper surface 302a of the body 302 to the lower surface 302b of the body 302. As in the suture guide 100, the first passage 312 extends from a first passage inlet 312a to a first passage outlet 312b and the second passage 314 extends from a second passage inlet 314a to a second passage outlet 314b. Therefore, the related description is not repeated but is understood to apply to the suture guide 300. The first passage 312 and the second passage 314 are, therefore, shaped, dimensioned, and contoured to provide guidance of a suture needle (not shown) from a first side of the suture guide 300 to a second side of the suture guide 300 to secure the suture guide 300 and any attached device to a patient.

Insertion of a suture material 402 is the same as described with respect to the suture material 202 described with respect to FIGS. 2D to 2F and will therefore not be repeated. In the example of the suture guide 300, a first end 408 of the suture material 402 includes a first securing device 406, which may be the same or similar as the first securing device 206. In the example of FIGS. 3A and 3B, the first securing device 406 is a bumper. The suture guide 300 includes a second securing device at a second end 410 of the suture material 402. The second securing device may be a wedge 316 that is embedded into the suture guide 300. As shown in FIG. 3B, when the suture material 402 is extended through the suture guide 300 (e.g., and tension is applied with a tool 450), instead of tying a knot or applying a bumper to the second end 410, the wedge 316 may be depressed, pushed, or otherwise moved to intersect the second passage 314 and the suture material 402 therein. In this manner, the suture material 402 is secured within the second passage 314 and is prevented from movement. Additionally, or alternatively, the second securing device may be a clip 318 to prevent movement of the suture material 402 at the second end 410. Any of a knot, bumper, clip, or pre-embedded wedge may be applied to the suture material at the second end as the second securing device, in either or both of the suture guide 300 or the suture guide 100.

In other words, the second side of the suture material 402 (or the suture material 202), e.g., the outflow side, having traversed both passages 312, 314 of the channel and the subcutaneous passage (e.g., the patient suture passage 52 within the patient 50), can be secured in a number of manners. The securing of the outflow side occurs once the suture material 402 is pulled taut so that the first securing device 406 is seated at the first side, e.g., the inflow side. At that point, either a clip could be attached producing the desired level of tension of the suture material 402, or a pre-embedded wedge is advanced in a way that crimps the suture material within the channel, also providing the appropriate level of suture tension.

Figure 4:
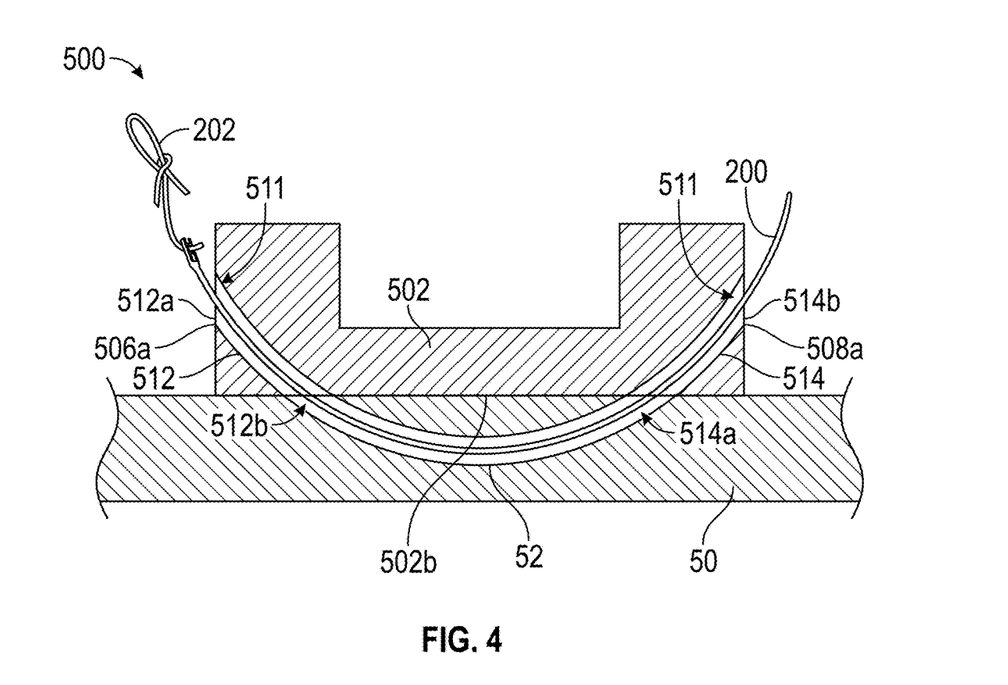
FIG. 4 illustrates a cross-sectional view of another exemplary suture guide, taken through a longitudinal centerline axis of the suture guide, according to the present disclosure.

FIG. 4 illustrates another exemplary suture guide 500. The suture guide 500 is substantially the same as the suture guide 100 shown in FIGS. 2A to 2F. Accordingly, like illustrated items represent the same features and are not discussed further herein, though it is understood that the same description and same alternatives apply to FIG. 4 as well. The suture guide 500 has a body 502 and a needle channel 511 having a first passage 512 and a second passage 514.

In the suture guide 500 of FIG. 4, instead of entering through the top surface (as in FIGS. 2A to 2F), the first passage 512 has a first passage inlet 512a on a side surface 506a of the suture guide 500. The first passage 512 has a first passage outlet 512b at a bottom surface 502b of the suture guide 500. Likewise, the second passage 514 has a second passage inlet 514a on the bottom surface 502b and a second passage outlet 514*b* on a side surface 508*a* of the suture guide 500. Although the shape of the suture guide passages is different as compared to the above examples, the conformance of the suture needle shape and the passage shape is the same such that the suture needle 200 causes the patient suture passage 52 in the patient 50 and is also caused to be advanced through the suture guide 500 in the same manner as described previously.

In any of the suture guides 100, 300, or 500 removal is facilitated by simply pulling on a tail of the suture material extending from the bumper, sufficient to allow the suture material on the deep side of the bumper to be severed, releasing the suture and the suture guide (and thus the catheter) from the skin surface.

Alternatively, when it is desired to remove the suture guides 100, 300, or 500 from the patient, the wedge may be retracted, the clip may be removed, any of the knots or bumpers may be cut or disconnected, or any combination thereof, such that the suture material (e.g., suture material 202 and suture material 402) can be removed from the passages and, thus, from the patient, to allow the suture guide to be removed from the patient.

Accordingly, the present disclosure provides a suture guide in which the shape, angle, contour, or configuration of the needle tract (e.g., the passage) guides the suture needle to a specific location. In this description, the specific location is a second side of the suture guide that is on an opposing side of a catheter (or on an opposing side of the location in which the catheter will be secured, if not yet secured. The aforementioned disclosure provides a tract or contour that includes not only the passages provided in the suture guide, but also a portion within the patient. In this sense, the passages (e.g., 112, 114 or 312, 314 or 512, 514) and the patient suture passage 52 form a needle path. Thus, the needle tract is not entirely within the suture guide. The suture guide of the present disclosure provides a pair of separate needle tracts (e.g., the passages) designed to direct a suture needle in the front, and out of the back of one part of the suture guide, traversing the patient tissue below the skin surface (therefore completely extrinsic to the suture guide), and then re-entering at a specific point in a separate part of the suture guide. The suture guide of the present disclosure is provided entirely above the skin surface of the patient. Thus, the needle channel comprises a first passage and a second passage that are completely separate and interrupted by a traversal through the patient's tissue.

Accordingly, the suture guides of the present disclosure provide a needle tract from a first side of the catheter to a second side of the catheter that is free from structure within the patient. That is, there is no structural channel or passage formed by a device within the patient. Instead, the channel formed by the passages above the surface of the patient causes a predetermined path within the patient to be traversed by the suture needle and suture material. In this sense, the pathway through the patient may be considered as a virtual channel, that is, predetermined channel or path caused to be traversed by the needle, but without a structural boundary.

Aspects of the present disclosure may be appreciated from the following clauses.

A suture guide for securing a catheter to a patient, the suture guide comprising a body having an upper surface, a lower surface, a first side surface extending between the upper surface and the lower surface, and a second side surface extending on an opposing side of the body between the upper surface and the lower surface, and a needle channel extending through the body, the needle channel comprising a first passage extending from a first passage inlet to a first passage outlet, and a second passage extending from a second passage inlet a second passage outlet, wherein the first passage is curved toward the second passage as the first passage extends from the first passage inlet to the first passage outlet, and wherein the first passage is configured to guide a suture needle from the first passage outlet to the second passage inlet such that the suture needle exits the first passage, traverses skin and tissue of a patient to create a patient suture passage between the first passage and the second passage, and enters the second passage to secure the catheter to the patient.

The suture guide of the preceding clause, wherein a contour of the first passage is the same as a contour of the suture needle.

The suture guide of any preceding clause, wherein a contour of the second passage is the same as a contour of the suture needle.

The suture guide of any preceding clause, wherein a contour of the patient suture passage is the same as a contour of the suture needle.

The suture guide of any preceding clause, wherein the second passage is curved away from the first passage as the second passage extends from the second passage inlet to the second passage outlet.

The suture guide of any preceding clause, wherein the first passage outlet and the second passage inlet are located on the lower surface of the body.

The suture guide of any preceding clause, wherein the first passage inlet and the second passage outlet are located on the upper surface of the body.

The suture guide of any preceding clause, wherein the first passage inlet is located on the first side surface of the body, and the second passage outlet is located on the second side surface of the body.

The suture guide of any preceding clause, wherein the suture guide comprises a vertical centerline axis, and the first passage is on a first side of the vertical centerline axis and the second passage is on a second side of the vertical centerline axis.

The suture guide of any preceding clause, wherein the first passage outlet is closer to the vertical centerline axis than the first passage inlet.

A catheter assembly comprising a catheter; and a suture guide coupled to the catheter, the suture guide comprising a body having an upper surface, a lower surface, a first side surface extending between the upper surface and the lower surface, and a second side surface extending on an opposing side of the body between the upper surface and the lower surface, and a needle channel extending through the body, the needle channel comprising a first passage on a first side of the catheter and extending from a first passage inlet to a first passage outlet, and a second passage on a second side of the catheter extending from a second passage inlet a second passage outlet, wherein the first passage is curved toward the second passage as the first passage extends from the first passage inlet to the first passage outlet, and wherein the first passage is configured to guide a suture needle from the first passage outlet to the second passage inlet such that the suture needle exits the first passage, traverses skin and tissue of a patient to create a patient suture passage between the first passage and the second passage, and enters the second passage to secure the catheter to the patient.

The catheter assembly of the preceding clause, wherein a contour of the first passage is the same as a contour of the suture needle.

The catheter assembly of any preceding clause, wherein a contour of the second passage is the same as a contour of the suture needle.

The catheter assembly of any preceding clause, wherein a contour of the patient suture passage is the same as a contour of the suture needle.

The catheter assembly of any preceding clause, wherein the second passage is curved away from the first passage as the second passage extends from the second passage inlet to the second passage outlet.

The catheter assembly of claim 11, wherein the first passage outlet and the second passage inlet are located on the lower surface of the body.

The catheter assembly of any preceding clause, wherein the first passage inlet and the second passage outlet are located on the upper surface of the body.

The catheter assembly of any preceding clause, wherein the first passage inlet is located on the first side surface of the body, and the second passage outlet is located on the second side surface of the body.

The catheter assembly of any preceding clause, wherein the suture guide comprises a vertical centerline axis, and the first passage is on a first side of the vertical centerline axis and the second passage is on a second side of the vertical centerline axis.

The catheter assembly of any preceding clause, wherein the first passage outlet is closer to the vertical centerline axis than the first passage inlet.

A suture guide for securing a catheter to a patient, the suture guide comprising a body having an upper surface, a lower surface, a first side surface extending between the upper surface and the lower surface, and a second side surface extending on a opposing side of the body between the upper surface and the lower surface and a needle channel. The needle channel includes a first passage extending from a first passage inlet to a first passage outlet and a second passage separate from the first passage, the second passage extending from a second passage inlet a second passage outlet. The needle channel is configured to guide a suture needle from the first passage inlet to the second passage outlet such that the suture needle traverses skin and tissue of a patient between the first passage and the second passage and such that a contour of the first passage, a contour of the second passage, and a contour of the tissue traversed by the suture needle is the same as a contour of the suture needle.

The suture guide of the preceding clause, wherein the second passage inlet is configured to guide the suture needle from the skin and tissue of the patient into the second passage.

The suture guide of any preceding clause, wherein the first passage outlet is configured to guide the suture needle from the first passage, through the skin and the tissue of the patient, and into the second passage.

The suture guide of any preceding clause, wherein the second passage inlet is larger than the second passage outlet.

The suture guide of any preceding clause, wherein the first passage inlet and the second passage outlet are both located on the upper surface of the body.

The suture guide of any preceding clause, wherein the upper surface is non-planar.

The suture guide of any preceding clause, wherein the first passage outlet and the second passage inlet are both located on the lower surface of the body.

The suture guide of any preceding clause, wherein the lower surface is non-planar.

The suture guide of any preceding clause, wherein the first passage and the second passage are both configured to guide the suture needle from the first passage inlet to the second passage outlet.

The suture guide of any preceding clause, wherein the suture guide comprises a longitudinal centerline extending from the upper surface to the lower surface, and wherein the first passage and the second passage are on opposing sides of the longitudinal centerline.

The suture guide of any preceding clause, wherein the first passage inlet and the second passage outlet are on opposing sides of the longitudinal centerline.

The suture guide of any preceding clause, wherein the first passage outlet and the second passage inlet are on opposing sides of the longitudinal centerline.

The suture guide of any preceding clause, wherein the needle channel is free from structure under the skin of the patient.

The suture guide of any preceding clause, wherein the needle channel forms a needle tract having the needle channel and a virtual channel between the first passage and the second passage.

The suture guide of any preceding clause, wherein the needle channel is free from structure between the first passage outlet and the second passage inlet.

The suture guide of any preceding clause, wherein the first passage outlet and the second passage inlet are located on the same surface of the body.

The suture guide of any preceding clause, wherein the first passage inlet and the second passage outlet are located on the upper surface of the body.

The suture guide of any preceding clause, wherein the first passage inlet is located on the first side surface and the second passage outlet is located on the second side surface.

The suture guide of any preceding clause, wherein the first passage does not enter and exit on the same surface of the body.

The suture guide of any preceding clause, wherein the second passage does not enter and exit on the same surface of the body.

A catheter assembly including the suture guide of any preceding clause.

A catheter assembly includes a catheter and a suture guide coupled to the catheter, the suture guide having a needle tract configured to guide a suture needle from a first side of the catheter to a second, opposing side of the catheter. The needle tract is configured to guide the suture needle through the suture guide and through a patient's skin and tissue to secure the catheter to the patient's skin.

The catheter assembly of any preceding clause, wherein an inlet to the needle tract and an outlet to the needle tract are on the same surface of the suture guide.

The catheter assembly of any preceding clause, wherein the needle tract is formed of a first passage, a second passage separate from the first passage, and a space in between the first passage and second passage that is outside of a body of the suture guide and traverses the patient's skin.

The catheter assembly of any preceding clause, wherein the needle tract includes a virtual channel between the first passage and the second passage.

The catheter assembly of any preceding clause, wherein the needle tract is free from structure between an outlet of the first passage and an inlet of the second passage.

The catheter assembly of any preceding clause, wherein the catheter and the suture guide are integrally formed.

The catheter assembly of any preceding clause, wherein the catheter is removably coupled to the suture guide.

The catheter assembly of any preceding clause, wherein the catheter is permanently affixed to the suture guide.

The catheter assembly of any preceding clause, wherein the needle tract is free from structure under the skin of the patient.

A method of securing a suture guide of any preceding clause.

A method of inserting a catheter assembly of any preceding clause.

A method for securing a catheter to a patient includes locating a suture guide on a skin surface of the patient, inserting a suture needle with suture material affixed thereto into the suture guide, guiding the suture needle from a first side of the suture guide to a second, opposing side of the suture guide, wherein the first side and the second, opposing side are both located above the skin surface of the patient, and securing the suture material such that the suture guide is secured to the skin surface of the patient.

The method of any preceding clause, wherein locating the suture guide on the skin surface comprises placing a lower surface of the suture guide on the skin surface.

The method of any preceding clause, wherein inserting the suture needle into the suture guide comprises inserting the suture needle into a first passage of the suture guide.

The method of any preceding clause, further comprising exiting the suture needle from a second passage of the suture guide, the second passage being separate from the first passage.

The method of any preceding clause, wherein guiding the suture needle comprises inserting the suture needle into a first passage in the suture guide, then extending the suture needle through the skin surface of the patient, and then extending the suture needle into a second passage in the suture guide.

The method of any preceding clause, wherein the suture needle exits the suture guide from the second passage.

The method of any preceding clause, wherein the first passage, tissue below the skin surface, and the second passage form a needle tract for the suture needle.

The method of any preceding clause, wherein securing the suture material comprises securing a first end of the suture material at the first side of the suture guide and securing a second end of the suture material at the second, opposing side of the suture guide.

The method of any preceding clause, wherein securing the first end of the suture material comprises providing a pre-tied or pre-located bumper on the first end of the suture material.

The method of any preceding clause, wherein securing the second end of the suture material comprises tying the second end of the suture material.

The method of any preceding clause, wherein securing the second end of the suture material comprises depressing a wedge to secure the suture material within the suture guide.

The method of any preceding clause, wherein securing the second end of the suture material comprises attaching a clip to the second end of the suture material.

Although the foregoing description is directed to the preferred embodiments, it is noted that other variations and modifications will be apparent to those skilled in the art and may be made without departing from the spirit or scope of the disclosure. Moreover, features described in connection with one embodiment may be used in conjunction with other embodiments, even if not explicitly stated above.

The invention claimed is:

1. A suture guide assembly for securing a catheter to a patient, the suture guide assembly comprising: a suture needle; a suture guide comprising:
   a body having an upper surface, a lower surface, a first side surface extending between the upper surface and the lower surface, and a second side surface extending on an opposing side of the body between the upper surface and the lower surface; and
   a needle channel extending through the body, the needle channel comprising:
      a first passage extending from a first passage inlet to a first passage outlet; and
      a second passage extending from a second passage inlet a second passage outlet,
   wherein the first passage is arcuate and is curved toward the second passage as the first passage extends from the first passage inlet to the first passage outlet,
   wherein the second passage is arcuate and is curved away from the first passage as the second passage extends from the second passage inlet to the second passage outlet, and
   wherein the first passage is configured to guide the suture needle with a suture material from the first passage outlet to the second passage inlet such that the suture needle exits the first passage through the first passage outlet, traverses skin and tissue of a patient to create a patient suture passage between the first passage and the second passage, entirely exits the skin and the tissue of the patient, enters the second passage, and entirely exits the second passage through the second passage outlet while the suture material remains in the skin and the tissue of the patient to secure the catheter to the patient.

2. The suture guide assembly of claim 1, wherein a contour of the first passage is the same as a contour of the suture needle.

3. The suture guide assembly of claim 1, wherein a contour of the second passage is the same as a contour of the suture needle.

4. The suture guide assembly of claim 1, wherein a contour of the patient suture passage is the same as a contour of the suture needle.

5. The suture guide assembly of claim 1, wherein the first passage outlet and the second passage inlet are located on the lower surface of the body.

6. The suture guide assembly of claim 1, wherein the first passage inlet and the second passage outlet are located on the upper surface of the body.

7. The suture guide assembly of claim 1, wherein the first passage inlet is located on the first side surface of the body, and the second passage outlet is located on the second side surface of the body.

8. The suture guide assembly of claim 1, wherein the suture guide comprises a vertical centerline axis, and the first passage is on a first side of the vertical centerline axis and the second passage is on a second side of the vertical centerline axis.

9. The suture guide assembly of claim 8, wherein the first passage outlet is closer to the vertical centerline axis than the first passage inlet.

10. A catheter assembly comprising:
   a catheter extending along a longitudinal centerline axis; and
   a suture guide coupled to the catheter, the suture guide having a vertical centerline axis and comprising:
      a body having an upper surface, a lower surface, a first side surface extending between the upper surface and the lower surface, and a second side surface extending on an opposing side of the body between the upper surface and the lower surface;
a groove in the body, the catheter disposed in the groove such that the longitudinal centerline axis of the catheter is substantially perpendicular to the vertical centerline axis and the catheter is substantially horizontal with respect to the suture guide; and
a needle channel extending through the body, the needle channel comprising:
  a first passage on a first side of the catheter and extending from a first passage inlet to a first passage outlet, the first passage inlet and the first passage outlet being substantially parallel with the vertical centerline axis; and
  a second passage on a second side of the catheter extending from a second passage inlet a second passage outlet, the second passage inlet and the second passage outlet being substantially parallel with the vertical centerline axis,
wherein the first passage is curved toward the second passage as the first passage extends from the first passage inlet to the first passage outlet, and
wherein the first passage is configured to guide a suture needle from the first passage outlet to the second passage inlet such that the suture needle exits the first passage, traverses skin and tissue of a patient to create a patient suture passage between the first passage and the second passage, and enters the second passage to secure the catheter to the patient.

11. The catheter assembly of claim 10, wherein a contour of the first passage is the same as a contour of the suture needle.

12. The catheter assembly of claim 10, wherein a contour of the second passage is the same as a contour of the suture needle.

13. The catheter assembly of claim 10, wherein a contour of the patient suture passage is the same as a contour of the suture needle.

14. The catheter assembly of claim 10, wherein the second passage is curved away from the first passage as the second passage extends from the second passage inlet to the second passage outlet.

15. The catheter assembly of claim 10, wherein the first passage outlet and the second passage inlet are located on the lower surface of the body.

16. The catheter assembly of claim 10, wherein the first passage inlet and the second passage outlet are located on the upper surface of the body.

17. The catheter assembly of claim 10, wherein the first passage inlet is located on the first side surface of the body, and the second passage outlet is located on the second side surface of the body.

18. The catheter assembly of claim 10, wherein the suture guide comprises the vertical centerline axis, and the first passage is on a first side of the vertical centerline axis and the second passage is on a second side of the vertical centerline axis.

19. The catheter assembly of claim 18, wherein the first passage outlet is closer to the vertical centerline axis than the first passage inlet.

* * * * *